US008409863B2

(12) United States Patent
Natan et al.

(10) Patent No.: US 8,409,863 B2
(45) Date of Patent: Apr. 2, 2013

(54) NANOPARTICULATE CHEMICAL SENSORS USING SERS

(75) Inventors: Michael J. Natan, Los Altos, CA (US); Marcelo Eduardo Piotti, San Jose, CA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 232 days.

(21) Appl. No.: 11/611,052

(22) Filed: Dec. 14, 2006

(65) Prior Publication Data
US 2007/0259437 A1 Nov. 8, 2007

Related U.S. Application Data

(60) Provisional application No. 60/825,676, filed on Sep. 14, 2006, provisional application No. 60/750,763, filed on Dec. 14, 2005.

(51) Int. Cl.
*G01N 33/20* (2006.01)
*G01N 33/00* (2006.01)

(52) U.S. Cl. .............................. 436/79; 436/80; 436/171

(58) Field of Classification Search .................... 436/79, 436/171, 80; 422/82.05, 82.02, 68.1, 50
See application file for complete search history.

(56) References Cited

U.S. PATENT DOCUMENTS

| 3,975,084 A | 8/1976 | Block |
| 4,039,297 A | 8/1977 | Takenaka |
| 4,313,734 A | 2/1982 | Leuvering |
| 4,802,761 A | 2/1989 | Bowen et al. |
| 4,853,335 A | 8/1989 | Olsen et al. |
| 4,920,059 A | 4/1990 | Moeremans et al. |
| 5,023,139 A | 6/1991 | Birnboim et al. |
| 5,059,394 A | 10/1991 | Phillips et al. |
| 5,096,809 A | 3/1992 | Chen et al. |
| 5,112,127 A | 5/1992 | Carrabba et al. |
| 5,137,827 A | 8/1992 | Mroczkowski et al. |
| 5,255,067 A | 10/1993 | Carrabba et al. |
| 5,266,498 A | 11/1993 | Tarcha et al. |
| 5,384,265 A | 1/1995 | Kidwell et al. |
| 5,441,894 A | 8/1995 | Coleman et al. |
| 5,445,972 A | 8/1995 | Tarcha et al. |
| 5,552,086 A | 9/1996 | Siiman et al. |
| 5,567,628 A | 10/1996 | Tarcha et al. |
| 5,580,492 A | 12/1996 | Bonnemann et al. |
| 5,609,907 A | 3/1997 | Natan |
| 5,637,508 A | 6/1997 | Kidwell et al. |
| 5,674,699 A | 10/1997 | Saunders et al. |
| 5,825,790 A | 10/1998 | Lawandy |

(Continued)

FOREIGN PATENT DOCUMENTS

| EP | 0 653 625 | 5/1995 |
| EP | 0 703 454 | 3/1996 |

(Continued)

OTHER PUBLICATIONS

Michaels, Amy M., et al. Ag Nanocrystal Junctions as the Site for Surface-Enhanced Raman Scattering of Single Rhodaine 6G Molecules, J. Phys. Chem. B 2000, 104, 11965-11971.*

(Continued)

*Primary Examiner* — Christine T Mui
(74) *Attorney, Agent, or Firm* — Mark Lindsey

(57) ABSTRACT

A system to selectively deliver relatively small analyte molecules of interest to a SERS-active nanoparticle surface while excluding dozens to hundreds of other species in the environment. In particular, the present invention provides a permselective film that renders the particles of interest as viable small molecule optically addressable sensors.

10 Claims, 3 Drawing Sheets

Structure and function of nanofilters: SERS-active nanoparticles coated with permselective thin films, and responses to analytes and interferants.

U.S. PATENT DOCUMENTS

| | | | |
|---|---|---|---|
| 5,828,450 A | 10/1998 | Dou et al. | |
| 5,833,924 A | 11/1998 | McClintock et al. | |
| 5,864,397 A | 1/1999 | Vo-Dinh | |
| 5,891,738 A | 4/1999 | Soini et al. | |
| 5,935,755 A | 8/1999 | Kazmaier et al. | |
| 5,958,704 A | 9/1999 | Starzl et al. | |
| 6,020,207 A | 2/2000 | Liu | |
| 6,027,890 A | 2/2000 | Ness et al. | |
| 6,103,868 A | 8/2000 | Heath et al. | |
| 6,136,610 A | 10/2000 | Polito et al. | |
| 6,149,868 A * | 11/2000 | Natan et al. | 422/82.05 |
| 6,200,820 B1 | 3/2001 | Hansen et al. | |
| 6,219,137 B1 | 4/2001 | Vo-Dinh | |
| 6,235,241 B1 | 5/2001 | Catt et al. | |
| 6,274,323 B1 | 8/2001 | Bruchez et al. | |
| 6,344,272 B1 | 2/2002 | Oldenburg et al. | |
| 6,361,944 B1 | 3/2002 | Mirkin et al. | |
| 6,422,998 B1 | 7/2002 | Vo-Dinh et al. | |
| 6,436,651 B1 | 8/2002 | Everhart et al. | |
| 6,451,619 B1 | 9/2002 | Catt et al. | |
| 6,500,622 B2 | 12/2002 | Bruchez, Jr. et al. | |
| 6,514,767 B1 * | 2/2003 | Natan | 436/166 |
| 6,514,770 B1 | 2/2003 | Sorin | |
| 6,558,956 B1 | 5/2003 | Carron et al. | |
| 6,562,403 B2 | 5/2003 | Klabunde et al. | |
| 6,587,197 B1 | 7/2003 | Rahbar-Dehghan | |
| 6,595,427 B1 | 7/2003 | Soni et al. | |
| 6,603,537 B1 | 8/2003 | Dietz et al. | |
| 6,610,351 B2 | 8/2003 | Shchegolikhin et al. | |
| 6,630,307 B2 | 10/2003 | Bruchez et al. | |
| 6,642,012 B1 | 11/2003 | Ashdown | |
| 6,646,738 B2 | 11/2003 | Roe | |
| 6,649,138 B2 | 11/2003 | Adams et al. | |
| 6,653,080 B2 | 11/2003 | Bruchez et al. | |
| 6,682,596 B2 | 1/2004 | Zehnder et al. | |
| 6,687,395 B1 | 2/2004 | Dietz et al. | |
| 6,699,724 B1 | 3/2004 | West et al. | |
| 6,730,400 B1 | 5/2004 | Komatsu et al. | |
| 6,743,581 B1 | 6/2004 | Vo-Dinh | |
| 6,750,016 B2 | 6/2004 | Mirkin et al. | |
| 6,750,031 B1 | 6/2004 | Ligler et al. | |
| 6,759,235 B2 | 7/2004 | Empedocles et al. | |
| 6,778,316 B2 | 8/2004 | Halas et al. | |
| 6,815,064 B2 | 11/2004 | Treadway et al. | |
| 6,815,212 B2 | 11/2004 | Ness et al. | |
| 6,838,243 B2 | 1/2005 | Lai et al. | |
| 6,861,263 B2 | 3/2005 | Natan | |
| 6,919,009 B2 | 7/2005 | Stonas et al. | |
| 6,970,246 B2 | 11/2005 | Hansen | |
| 6,972,173 B2 | 12/2005 | Su et al. | |
| 7,045,049 B1 | 5/2006 | Natan et al. | |
| 7,079,241 B2 | 7/2006 | Empedocles et al. | |
| 7,098,041 B2 | 8/2006 | Kaylor et al. | |
| 7,102,747 B2 | 9/2006 | Wang et al. | |
| 7,102,752 B2 | 9/2006 | Kaylor et al. | |
| 7,105,310 B1 | 9/2006 | Gray et al. | |
| 7,122,384 B2 | 10/2006 | Prober et al. | |
| 7,123,359 B2 | 10/2006 | Armstrong et al. | |
| 7,141,212 B2 | 11/2006 | Catt et al. | |
| 7,192,778 B2 | 3/2007 | Natan | |
| 7,443,489 B2 | 10/2008 | Natan | |
| 2002/0142480 A1 * | 10/2002 | Natan | 436/171 |
| 2003/0232388 A1 | 12/2003 | Kreimer et al. | |
| 2005/0036148 A1 | 2/2005 | Phelan | |
| 2005/0037510 A1 | 2/2005 | Sharrock et al. | |
| 2005/0037511 A1 | 2/2005 | Sharrock | |

FOREIGN PATENT DOCUMENTS

| | | |
|---|---|---|
| EP | 1 181 091 | 2/2002 |
| WO | WO 88/07680 | 10/1988 |
| WO | WO 92/17781 | 10/1992 |
| WO | WO 98/04740 | 2/1998 |
| WO | WO 98/10289 | 3/1998 |
| WO | WO 99/21934 | 5/1999 |
| WO | WO 00/11024 | 3/2000 |
| WO | WO 00/27645 | 5/2000 |
| WO | WO 01/08081 | 2/2001 |
| WO | WO 01/25002 | 4/2001 |
| WO | WO 01/25510 | 4/2001 |
| WO | WO 01/25758 | 4/2001 |
| WO | WO 02/29136 | 4/2002 |
| WO | WO 02/068932 | 6/2002 |
| WO | WO 02/079764 | 10/2002 |
| WO | WO 03/021231 | 3/2003 |
| WO | WO 03/021853 | 3/2003 |
| WO | WO 2006/036130 | 4/2006 |
| WO | WO 2006/042111 | 4/2006 |
| WO | WO 2006/105110 | 10/2006 |

OTHER PUBLICATIONS

Liz-Marzan Luis M., et al. Synthesis of Nanosized Gold-Silica Core-Shell Particles, Langmuir, 1996, 12, 4329-4335.*

Khlebtsov, N.G., Optical models for conjugates of gold and silver nanoparticles with biomacromolecules, Journal of Quantitative Spectroscopy & Radiative Transfer, 2004, 89, 143-153.*

U.S. Appl. No. 09/598,395, filed Jun. 20, 2000, Natan et al.

U.S. Appl. No. 09/676,890, filed Oct. 2, 2000, Natan et al.

U.S. Appl. No. 09/677,198, filed Oct. 2, 2000, Natan et al.

Akbarian F. et al., "Porous Sol-Gel Silicates Containing Gold Particles as Matrices for Surface-Enhanced Raman Spectroscopy", Journal of Raman Spectroscopy; vol. 27, Issue 10, Oct. 1996, pp. 775-783.

Akerman et al., "Nanocrystal targeting in vivo" PNAS, 99 (20), 2002, p. 12621.

Ascencio et al, "A truncated icosahedral structure observed in gold nanoparticles", Jorge A. Ascencio, Mario Surface Science, vol. 447, Issues 1-3, Feb. 20, 2000, pp. 73-80.

Averitt et al., "A metal nanoshell consists of a nanometer-scale dielectric core surrounded by a thin metallic shell. The plasmon resonance of metal nanoshells displays a geometric tunability", JOSA B, vol. 16, Issue 10, 1999, pp. 1824-1832.

Ballou et al., "Noninvasive imaging of quantum dots in mice", Bioconjugate Chem., 15 (1), 2004, pp. 79-86.

Brazdil et al., "Resonance Raman spectra of adsorbed species at solid-gas interfaces. Nitrosodimethylaniline adsorbed on silica and alumina surfaces", J. Phys. Chem., 1981, 85 (8), pp. 995-1004.

Bruchez et al., "Semiconductor nanocrystals as fluorescent biological labels", Science, Sep. 25, 1998, 281(5385), pp. 2013-2016.

Byahut et al., "Direct comparison of the chemical properties of single crystal Ag(111) and electrochemically roughened Ag as substrates for surface Raman scattering", Langmuir, 1991, 7 (3), pp. 508-513.

Chan et al., "Quantum dot bioconjugates for ultrasensitive nonisotopic detection", Science, 1998, 281, pp. 2016-2018.

Co-Pending U.S. Appl. No. 11/051,222, filed Feb. 4, 2005.
Co-Pending U.S. Appl. No. 11/113,601, filed Apr. 25, 2005.
Co-Pending U.S. Appl. No. 11/132,510, filed May 18, 2005.
Co-Pending U.S. Appl. No. 11/132,974, filed May 18, 2005.
Co-Pending U.S. Appl. No. 11/133,926, filed May 20, 2005.
Co-Pending U.S. Appl. No. 11/134,129, filed May 20, 2005.
Co-Pending U.S. Appl. No. 11/134,145, filed May 20, 2005.
Co-Pending U.S. Appl. No. 11/622,915, filed Jan. 12, 2007.
Co-Pending U.S. Appl. No. 12/245,538, filed Oct. 3, 2008.
Co-Pending U.S. Appl. No. 12/245,555, filed Oct. 3, 2008.

Dhere et al., "Twinned colloidal gold particles", Ultramicroscopy, vol. 18, Issues 1-4, 1985, pp. 415-417.

Duff et al., "The Morphology and Microstructure of Colloidal Silver and Gold Angewandte Chemie", International Edition in English, vol. 26, Issue 7, 1987, pp. 676-678.

El-Kouedi et al., "Optical Properties of Gold-Silver Nanoparticle Pair Structures", J. Phys. Chem. B, 104, 2000, pp. 4031-4037.

Emory et al., "Direct Observation of Size-Dependent Optical Enhancement in Single Metal Nanoparticles", Journal of the American Chemical Society, 1998, 120 (31), 8009-8010.

Emory et al., "Near-Field Surface-Enhanced Raman Spectroscopy on Single Silver Nanoparticles", Analytical Chemistry, 1997, 69 (14), pp. 2631-2635.

Emory et al., "Screening and Enrichment of Metal Nanoparticles with Novel Optical Properties", J. Phys. Chem. B, 1998, 102 (3), pp. 493-497.

European Patent Office, EP Supplementary Search Report prepared Apr. 18, 2008, for European Patent Application No. EP 05 85 6641, 4 pages.

Félidj et al., "A new approach to determine nanoparticle shape and size distributions of SERS-active gold-silver mixed colloids", New J. Chem., 1998, 22, pp. 725-732.

Freeman et al., "Ag-Clad Au Nanoparticles: Novel Aggregation, Optical, and Surface-Enhanced", Raman Scattering Properties, M.J, J. Phys. Chem., vol. 100, No. 2, 1996, pp. 718-724.

Gao et al., "In vivo cancer targeting and imaging with semiconductor quantum dots", Nature Biotechnology, 22 (8), 2004, pp. 969-976.

Grabar et al., "Preparation and Characterization of Au Colloid Monolayers", Analytical Chemistry, 1995, 67 (4), pp. 735-743.

Hall et al., "Cocondensation of Organosilica Hybrid Shells on Nanoparticle Templates: A Direct Synthetic Route to Functionalized Core-Shell Colloids", Langmuir, 2000, 16 (3), pp. 1454-1456.

Hoadk et al., "Laser-Induced Inter-Diffusion in AuAg Core-Shell Nanoparticles", J. Phys. Chem. B, 2000, vol. 104, pp. 11708-11718.

Horkans et al., "Pulsed Potentiostatic Deposition of Gold from Solutions of the Au(I) Sulfite Complex", Electrochem. Soc., 124, 1977, p. 1499.

Hua-Zhong Yu et al., "Surface-Enhanced Raman Scattering (SERS) from Azobenzene Self-Assembled Sandwiches", Langmuir, vol. 15, No. 1, 1999, pp. 16-19.

Jin et al., "Photoinduced Conversion of Silver Nanospheres to Nanoprisms", Science, Nov. 30, 2001, 294, pp. 1901-1903.

Keating et al., "Heightened Electromagnetic Fields Between Metal Nanoparticles: Surface Enhanced Raman Scattering from Metal-Cytochrome c-Metal Sandwiches", J. Phys. Chem. B, vol. 102, No. 47, 1998, pp. 9414-9425.

Keating et al., "Protein: Colloid Conjugates for Surface Enhanced Raman Scattering: Stability and Control of Protein Orientation", J. Phys. Chem. B, vol. 102, No. 47, 1998, pp. 9404-9413.

Kneipp et al., "Approach to Single Molecule Detection Using Surface-Enhanced Resonance Raman Scattering (SERRS): A Study Using Rhodamine 6G on Colloidal Silver", Applied Spectroscopy, vol. 49, Issue 6, pp. 12A-20A and 691-860, Jun. 1995, pp. 780-784.

Kneipp et al., "Detection and identification of a single DNA base molecule using surface-enhanced Raman scattering (SERS)", Rev. E 57, 1998, pp. R6281-R6284.

Kneipp et al., "Extremely Large Enhancement Factors in Surface-Enhanced Raman Scattering for Molecules on Colloidal Gold Clusters", Applied Spectroscopy, vol. 52, Issue 12, pp. 443A-455A and 1493-1626, Dec. 1998, pp. 1493-1497.

Kneipp et al., "Population Pumping of Excited Vibrational States by Spontaneous Surface-Enhanced Raman Scattering", Phys. Rev. Lett. 76, 1996, pp. 2444-2447.

Kneipp et al., "Single Molecule Detection Using Surface-Enhanced Raman Scattering (SERS)", Phys. Rev. Lett. 78, 1997, pp. 1667-1670.

Kneipp et al., "Single-Molecule Detection of a Cyanine Dye in Silver Colloidal Solution Using Near-Infrared Surface-Enhanced Raman Scattering", Applied Spectroscopy, vol. 52, Issue 2, pp. 72A-73A and 175-321, Feb. 1998, pp. 175-178.

Kneipp et al., "Surface-enhanced Raman scattering: A new tool for biomedical spectroscopy", Current Science, vol. 77, No. 7, Oct. 1999, pp. 915-926.

Kneipp et al., "Ultrasensitive Chemical Analysis by Raman Spectroscopy", Chem. Rev., 1999, 99 (10), pp. 2957-2976.

Kneipp, K., "High-sensitive SERS on colloidal silver particles in aqueous solution", Journal: Experimentelle Technik der Physik; vol. 36, No. 2, 1998, pp. 161-166.

Kovtyukhova et al., "Layer-by-Layer Assembly of Rectifying Junctions in and on Metal Nanowires", J. Phys. Chem. B, 2001, 105 (37), pp. 8762-8769.

Liz-Marzán et al., "Synthesis of Nanosized Gold-Silica Core-Shell Particles", Langmuir, 1996, 12 (18), pp. 4329-4335.

Lyon et al., "Confinement and Detection of Single Molecules in Submicrometer Channels", Analytical Chemistry, 1997, 69 (16), pp. 3400-3405.

Michaels et al., "Ag Nanocrystal Junctions as the Site for Surface-Enhanced Raman Scattering of Single Rhodamine 6G Molecules", J. Phys. Chem. B, 2000, 104 (50), pp. 11965-11971.

Michaels et al., "Surface Enhanced Raman Spectroscopy of Individual Rhodamine 6G Molecules on Large Ag Nanocrystals", J. Am. Chem. Soc., 1999, 121 (43), pp. 9932-9939.

Moskovits et al., "SERS and the Single Molecule: Near Field Microscopy and Spectroscopy", SPIE, 2001, vol. 4258, pp. 43-49.

Mucic et al., "DNA-Directed Synthesis of Binary Nanoparticle Network Materials", J. Am. Chem. Soc., 120 (48), 1998, pp. 12674-12675.

Nicewarner Sr. et al., "Synthesis and characterization of well-defined metal nanoparticle-protein-metal nanoparticle sandwiches", Penn State University/University Pk//Pa/16802, Abstracts of Papers of The American Chemical Society, Aug. 23, 1998, vol. 216, 1, pp. 172-COLL.

Nicewarner-Peña et al., "Submicrometer Metallic Barcodes", Science, Oct. 5, 2001, 294, pp. 137-141.

Nie et al., "Probing Single Molecules and Single Nanoparticles by Surface-Enhanced Raman Scattering", Emory, Science, Feb. 21, 1997, vol. 275, No. 5303, pp. 1102-1106.

Nie, S., "Optical detection of single molecules; Annual Review of Biophysics and Biomolecular Structure", vol. 26, 1997, pp. 567-596.

Nikoobakht et al., "Preparation and Growth Mechanism of Gold Nanorods (NRs) Using Seed-Mediated Growth Method", Chem. Mater., 15, 2003, pp. 1957-1962.

Ron et al., "Self-Assembled Monolayers on Oxidized Metals. 2. Gold Surface Oxidative Pretreatment, Monolayer Properties, and Depression Formation", Langmuir, 14 (5), 1998, pp. 1116-1121.

Sandrock et al., "Synthesis and Second-Harmonic Generation Studies of Noncentrosymmetric Gold Nanostructures", J. Phys. Chem. B, 103, 1999, pp. 2668-2673.

Sandrock, "Synthesis and Linear Optical Properties of Nanoscopic Gold Particle Pair Structures", J. Phys. Chem. B, 103, 1999, pp. 11398-11406.

Shibata et al., "Preparation of Silica Microspheres Containing Ag Nanoparticles", Journal of Sol-Gel Science and Technology, vol. 11, No. 3, Aug. 1998, pp. 279-287.

Stöber et al., "Controlled growth of monodisperse silica spheres in the micron size range", Journal of Colloid and Interface Science, vol. 26, Issue 1, Jan. 1968, pp. 62-69.

Sun et al., "Fabrication of nanoporous single crystal mica templates for electrochemical deposition of nanowire arrays", Journal of Materials Science, vol. 35, No. 5, Mar. 2000, pp. 1097-1103.

Switzer et al., "Electrochemical Self-Assembly of Copper/Cuprous Oxide Layered Nanostructures", J. Am. Chem. Soc., 1998, 120 (14), pp. 3530-3531.

Ung et al., "Controlled Method for Silica Coating of Silver Colloids. Influence of Coating on the Rate of Chemical Reactions", Langmuir, 1998, 14 (14), pp. 3740-3748.

Van Duyne et al., "Atomic force microscopy and surface-enhanced Raman spectroscopy. I. Ag island films and Ag film over polymer nanosphere surfaces supported on glass", Chem. Phys., vol. 99, Issue 3, pp. 2101-2115.

Vo-Dinh, T., "Surface-enhanced Raman Spectroscopy using metallic nanostructures", Trends in Analytical Chemistry, vol. 17, No. 8-9, 1998, XP002314222.

Walton et al., "Particles for Multiplexed Analysis in Solution: Detection and Identification of Striped Metallic Particles Using Optical Microscopy", Analytical Chemistry, 74 (10), 2002, pp. 2240-2247.

Wasileski et al., "Surface-Enhanced Raman Scattering from Substrates with Conducting or Insulator Overlayers: Electromagnetic Model Predictions and Comparisons with Experiment", Applied Spectroscopy, 2000, vol. 54, pp. 761-772.

* cited by examiner

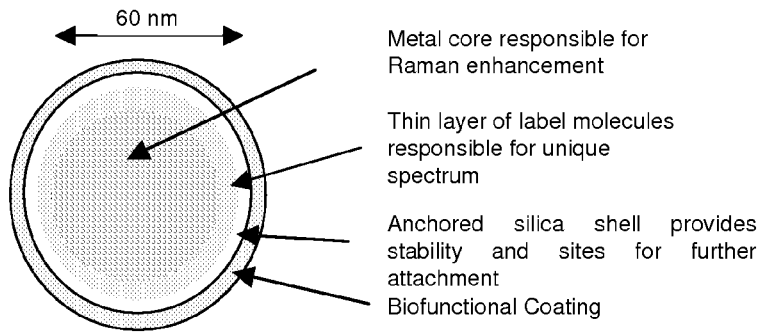
Figure 1. SERS nanotag structure
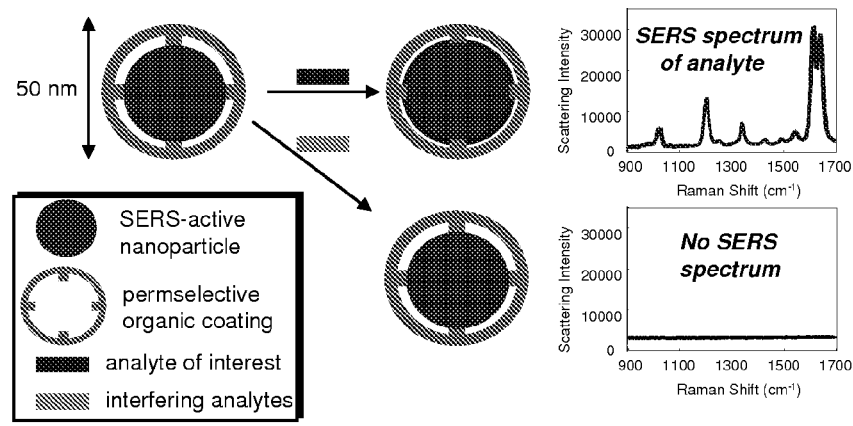
Figure 2. Structure and function of nanofilters: SERS-active nanoparticles coated with permselective thin films, and responses to analytes and interferants.
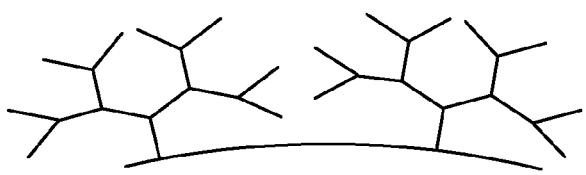
Figure 3. Single-point attached hyperbranched polymers

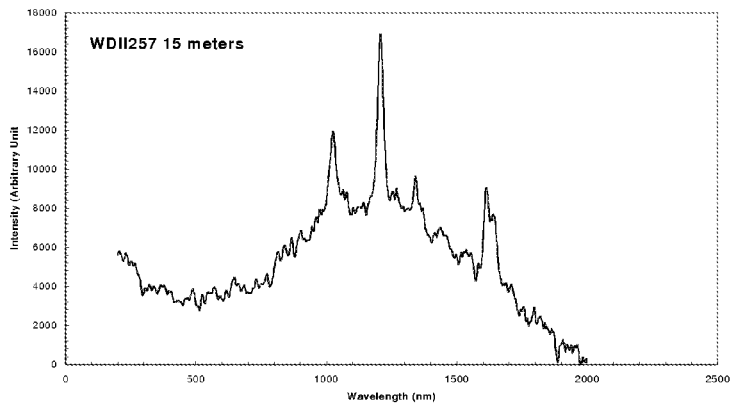
Figure 4. Standoff detection of SERS nanotags at 15 m, using a portable reader w/ 40 mW of 785 nm (data courtesy of System Planning Corp).
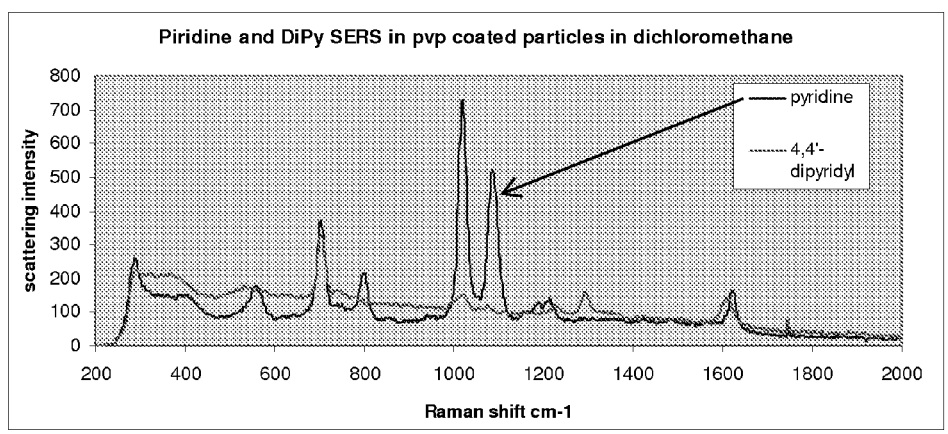
Figure 5.

NANOPARTICULATE CHEMICAL SENSORS USING SERS

RELATED APPLICATIONS

This application claims priority from U.S. Provisional Application Ser. No. 60/825,676, filed on Sep. 14, 2006, entitled "Nanoparticulate Chemical Sensors Using SERS" and from U.S. Provisional Application Ser. No. 60/750,763, filed on Dec. 14, 2005, entitled "Nanoparticulate Chemical Sensors Using SERS", the contents of each of which are incorporated herein in their entirety.

TECHNICAL FIELD

The present invention relates to a system combining permselective films and surface enhanced Raman scattering ("SERS")-active metal nanoparticles to make optically addressable, small-molecule chemical sensors.

BACKGROUND OF THE INVENTION

The development of methods and apparatus to detect small molecules using field-portable instrumentation is the ultimate goal of substantial research in the field of chemical analysis. In a research laboratory, small molecules are typically detected by gas chromatography (GC), liquid chromatography (LC), mass spectrometry (MS), or both (GC-MS, LC-MS). Despite intense effort, including efforts by the Defense Advanced Research Projects Agency ("DARPA"), over the past decade, miniaturization of this type of laboratory instrumentation while maintaining acceptable mass resolution and absolute sensitivity has proven impossible.

Field portable apparatus and methods for the detection of large molecules or proteins, cells, and DNA is possible. With respect to these large species, naturally-occurring detection molecules exist (such as antibodies or complementary sequences), to which detection tags (mostly optical) can be attached. Thus, 99% of all bioassays for these relatively large species involve a "sandwich" format, in which the analyte is immobilized by non-covalent interaction with a capture molecule, and quantified by non-covalent interaction with a labeled detection molecule.

Harnessing a New Detection Modality

Until recently, the only available optical detection tags were based on fluorescence. In U.S. Pat. No. 6,514,767, which patent is incorporated herein by reference in its entirety, Applicants described an optical detection tag based on surface enhanced Raman scattering ("SERS"). A tag consistent with the U.S. Pat. No. 6,514,767 patent is depicted in FIG. 1.[1] With SERS, molecules in very close proximity to nanoscale roughness features on noble metal surfaces (typically gold, silver or copper) or suitably-sized metal nanoparticles give rise to million- to trillion-fold increases [known as enhancement factor (EF)] in scattering efficiency.[2] With these tags, the SERS signal comes from submonolayers of reporter molecules sandwiched between the noble metal and a glass shell. In typical assays, the glass surface is coated with a biofuctional species that attaches to a bioanalyte of interest (e.g. an antibody for protein detection). These particles offer several significant advantages as optical detection tags: (i) they are excited in the near-infrared, eliminating the background visible fluorescence signal invariably associated with real-world measurements; (ii) different reporter molecules give rise to unique, narrow spectral features, allowing multiple signatures to be simultaneously detected; (iii) portable, robust and inexpensive instrumentation amenable to point-of-use implementation already exists; and (iv) exceptional sensitivity is possible.

Unfortunately, the SERS nanotags of FIG. 1 cannot be leveraged for detection of chemical warfare agents, e.g. sarin, because pairs of capture/detection molecules do not exist for low-molecular weight species, and more importantly, the Raman signal is (by design) locked in via the incorporation of a reporter molecule. Yet sarin and other low molecular weight species each have a distinctive SERS spectrum that could serve as a basis for ultrasensitive, accurate detection.

The present invention is directed toward overcoming one or more of the problems discussed above.

SUMMARY OF THE INVENTION

The present invention provides a system to selectively deliver relatively small analyte molecules of interest to a SERS-active nanoparticle surface while excluding dozens to hundreds of other species in the environment. In particular, the present invention provides a permselective film that renders the particles of interest as viable small molecule optically addressable sensors.

BRIEF DESCRIPTION OF THE DRAWINGS

FIG. 1 is a schematic representation of a SERS nanotag structure;

FIG. 2 is a schematic and graphical representation of the structure and function of SERS-active nanoparticles consistent with the present invention;

FIG. 3 is a schematic representation of single point attached hyperbranched polymers; and FIG. 4 is a graph of intensity as a function of wavelength depicting remote detection of SERS nanotags at 15 meters using a portable reader.

FIG. 5 is a graph of the SERS response of particles having permselective coatings in accordance with the present invention.

DETAILED DESCRIPTION OF THE INVENTION

Figure 6:
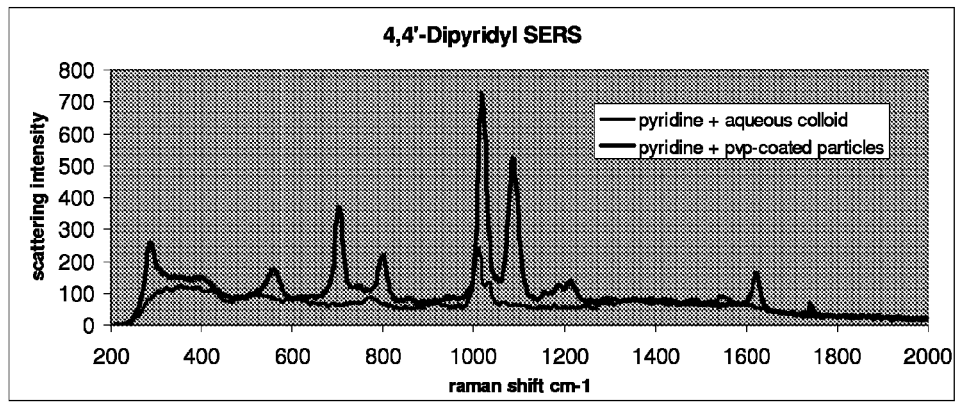
FIG. 6 is a graph of the SERS response of particles having permselective coatings in accordance with the present invention.

The difficulty experienced in prior attempts to develop portable systems for the detection of smaller molecules may be addressed with specially prepared SERS-active nanoparticles. In particular, particles may be coated with thin films that exhibit molecular recognition capabilities that permit passage of species of interest to the nanoparticle surface while rejecting unwanted entities. One such system is depicted in FIG. 2. Once the analytes of interest reach the noble metal (typically Au) surface of the particle, they adsorb and give rise to a unique Raman spectrum. The selectivity of the thin molecular filtering film, which could comprise either discrete molecules or polymeric species, need not be perfect: low-level binding of undesired species (interferants) can be detected (and accounted for) because of their distinct Raman spectra. Nanoparticles modified with permselective films are referred to herein as "SERS nanofilters".

Nanoparticles suitable for use as SERS nanofilters preferably have a maximum length of at most 300 nm and may be rod shaped, spherical, prisms, cubes arrowheads or other shapes. The nanoparticle will preferably have a diameter of less than 200 nm and most preferably between 40 nm and 100 nm. The nanoparticles have a spectroscopy active outer region. Typically, the outer region contains or is made of a metal such as Au, Ag, Cu, Na, K, Cr, Al, or Li.

The present invention also includes methods of manufacture of the SERS nanofilters and applications for their use. The present invention includes a method of detecting an analyte of interest by associating a SERS nanofilter as described herein with an analyte of interest in the presence of one or more interfering analytes. The detection method is predicated upon the permselective film allowing the analyte of interest to associate with the particle and preventing the interferent from associating with the particle. The method also includes obtaining a spectrum of the particle and associated analyte of interest.

The use of permselective films to selectively filter molecules, allowing certain ones to reach a surface while excluding others, is a well-established technique of analytical chemistry. Super-acoustic wave ("SAW") devices, Quartz Crystal microbalance ("QCM") sensors and especially electrochemical sensors are dependent on selective binding/rejection phenomena. Indeed, electrochemical detection of glucose in commercial products relies extensively on permselectivity of glucose, and rejection of electroactive interferants (e.g. ascorbate).

Appropriate surface coatings to create SERS nanofilters as described above and shown in FIG. 2 must exhibit five specific properties:

(1) The films must selectively allow specific analyte molecules (or classes of molecules) of interest to rapidly diffuse to the particle surface, where they can be detected by their unique SERS spectral signature. The ratio of partition coefficients for a specific analyte of interest and molecules with similar structures would ideally be at least 10:1, although other ratios may prove workable.

(2) The film must not use up all binding sites on the SERS-active nanoparticle. In other words, there must be surface adsorption sites available for analyte molecules that diffuse through the film.

(3) The film must be robust enough to survive during use in harsh, interferantladen environments.

(4) The Raman spectra of the films themselves must be simple and weak, because all spectral features of the film will comprise background noise above or through which the analyte spectrum must be detected.

(5) Attachment of the permselective film layers to the particles must be achievable without irreversible nanoparticle aggregation, which would lead to precipitation (and thus poor reproducibility).

Permselective Films

Suitable permselective coatings may consist of globular polymers (hyperbranched polymers) that are single-point attached to the particle surface as shown in FIG. 3. Such polymers could be of polar nature, and synthesized in aqueous conditions, or of non-polar character, generally prepared in organic solvents of lower polarity. The single point attachment would result in a "tree-like" structure of the polymer on the particle surface, providing a dense polymer coating while leaving available space on the noble metal particle surface for binding and detection of analytes of interest. The selective permeation of a hyperbranched film coating is governed by the structure, functionality and/or polarity of the polymers, and can potentially be tuned. For example, selective permeation based on molecular size might be based upon the characteristics of the "polymer trees" which would leave a small space between "branches" for smaller external molecules to go through and reach the metal surface, while large macromolecules or cells would be precluded from contacting the surface. In addition, non-polar or hydrophobic polymer coatings would act as a barrier for highly polar species (such as inorganic ions) while letting organic molecules penetrate the film layer. Accordingly, layered hyperbranched polymers with more than one permselectivity characteristic could be prepared, enabling "additive" filtration. Furthermore, the presence of specific functional groups at pre-defined locations in the polymers would be critical for controlling permeation selectivity via specific molecular interactions. This type of molecular recognition would be a pre-requisite for advancing the described technology from class-selective sensing to nanoparticle sensors tuned to distinct molecules within the class.

Several other types of films could potentially also be used to impart permselectivity. For example, polydimethylsiloxane (PDMS) has been shown to reject all ions from macroscopic SERS-active surfaces, while allowing candidate drug molecules to diffuse and adsorb (Mulvaney and Natan, unpublished results). Likewise, it may be possible to build porous glass films that exhibit permselectivity.

Films such as those described in *Hydrophobic Interaction of Analytes* with *Permselective Poly(N-vinyl amide) Films on Electrodes*[2,4] or the *Encyclopedia of Separation Science*[2B] may be suitable for use with chemical sensors based upon SERS nanofilters. The present invention is not limited to films such as those described in these references.

Single Molecule, Single-Particle SERS Has Been Demonstrated

Submonolayers of adsorbates on single particles have been shown to give rise to SERS spectra. The detection of single molecules by surface-enhanced Raman scattering (SERS) was first reported by two independent research groups in 1997.[3,4] Nie and coworkers detected rhodamine 6G (R6G) on immobilized silver nanoparticles that were either single particles or small aggregates. They took advantage of the additional resonance enhancement gained by exciting the sample within the electronic absorption band of R6G and used a screening method to rapidly locate particles that were SERS-active. Conversely, Kneipp's group intentionally aggregated colloidal silver in the presence of crystal violet (CV) and detected the aggregates as they diffused through the focal volume of a microscope objective. Coupled with Poisson statistics, they surmised that many of the SERS events they recorded were from single CV molecules. It was also noteworthy that they excited the sol with 830 nm light, well outside of CV's absorption band. Furthermore, they employed similar methods to detect single adenine molecules,[5] proving that single-molecule SERS detection was possible without taking advantage of additional resonance enhancement. Since that time, single-molecule SERS has been demonstrated on Au nanoparticles,[6] for hemoglobin[7] and for tyrosine.[8] Applicant has already been quite successful with the preparation of spherical SERS nanotags of FIG. 1, and it is well understood that anistropic noble metal nanoparticles (rods, prisms, cubes, arrowheads), in which the particle surface plasmon band is tuned to the near-IR excitation frequency, will give exponential increases in SERS brightness;[9].

Large-Scale Manufacture

Applicant currently manufactures colloidal Au nanoparticles in 1-2 liter batches, which provides approximately $10^{14}$ particles. A typical application of SERS tags (for example, for the detection of proteins or DNA) may involve $10^6$-$10^7$ particles, meaning that a single batch is capable of generating enough material for one million tests. Applicant is in the process of scaling up to 10-liter preparations. Moreover, very large scale manufacture of the core particles has been demonstrated commercially. For example, British Biocell International (BBI), a UK concern that supplies colloidal Au to diagnostic companies for use in lateral flow immunoassays, manufactures particles in 250-liter batches.

Because the polymeric coating on the particles contemplated and described above will be thin (i.e. 10 nm), small amounts of raw material will be needed. For example, to cover $10^{17}$ particles of 60-nm diameter with a 10-nm thick coating of a polymer of density 1 gm/cm$^3$ (an overestimate) would require only 1.6 grams of material.

Remote Detection of Raman Scattering

Recently, several groups[10-13] demonstrated remote Raman detection as a viable detection technique. This advancement follows from the recent availability of highly-sensitive light detectors and relatively low-cost pulsed laser systems, along with knowledge built from sophisticated lock-in amplifier-based Light Detection and Ranging ("LIDAR") systems, allowing for ultra-sensitive detection in ambient light conditions. For instance, Lawrence Livermore National Laboratory has explored passive detection of high-explosives using an 8" Schmidt-cassegrain telescope coupled to an f/1.8 spectrograph.[11] They were able to detect the Raman signal from TNT, RDX, PETN, and other nitrate/chlorate simulants embedded in a dry silica matrix at 50 meters with reasonable signal-to-noise ratios. Further development by this group[12] generated a remote imaging Raman system which achieved detection of calcite, TiO2, and gypsum at approximately 1 cm$^{-1}$ resolution at a 15 m distance using an AOTF (acousto-optical tunable filter)-based pulsed laser system.

Standoff Detection Has Already Been Demonstrated with SERS Nanotags

Due to large enhancement factors, SERS nanotags exhibit extremely strong signals compared to normal Raman spectra of solids or liquids. Accordingly, standoff detection of particles such as those produced by Applicant is becoming routine. See, for example, the graph of detection intensity as a function of wavelength included in FIG. 4. Importantly, the reporter molecules used in SERS tags are not resonantly enhanced, rather the SERS spectrum is merely obtained from a submonolayer of adsorbate. Thus, the SERS spectral intensity to be expected from analytes captured and detected with the proposed SERS nanofilters should be of similar magnitude.

Other Applications

While the initial application contemplated for the nanoparticulate chemical sensors of the present application may be the detection of chemical warfare agents, optically-detected, ultrasensitive detection of low molecular weight species is also of tremendous importance in bioanalysis. For example, the entire field of "metabolomics" is concerned with identification and quantition of the many hundreds of small molecules present in serum, many of these metabolites change in response to disease progression and/or therapeutic intervention. At present, the only way to analyze serum for these biomarkers is by LC-MS, which is slow, expensive, and not portable. The ability to design sensor particles for specific analytes that, by virtue of near-IR excitation, could be used in whole blood, would be of clinical significance.

Particles as described herein could also make up part of a system for air sampling at airport or other security checkpoints, where detection of explosives, narcotics or other agents, including substances on a passenger's skin, might be facilitated. In addition, in vivo imaging where the particles might be used to track the distribution of drug in living systems may be another possible application of the particles described herein.

Relevant References

1. U.S. Pat. No. 6,514,767, "Surface enhanced spectroscopy-active composite nanoparticles," issued Feb. 4, 2003.
2. Campion, A.; Kambhampati, P. Chem. Soc. Rev. 1998, 27, 241-249.
2A. Hofbauer, M; Heineman, W.; Kreischman, G; Steckhan, E.; "Hydrophobic Interaction of Analytes with Permselective Poly(N-vinyl amide) Films on Electrodes" Anal. Chem. 1999, 71, 399-406.
2B. Wilson, Ian; Poole, Colin; Cooke, Michael, eds., Encyclopedia of Separation Science, Academic Press (2000).
3. Nie, S.; Emory, S. R. Science. 1997, 275, 1102-1106.
4. Kneipp, K.; Wang, Y.; Kneipp, H.; Perelman, L. T.; Itzkan, I.; Dasari, R. R.; Feld, M. S. Phys. Rev. Lett. 1997, 78, 1667-1670.
5. Kneipp K, Kneipp H, Kartha V B, Manoharan R, Deinum G, Itzkan I, Dasari R R, Feld MS. Phys. Rev. E 1998; 57: R6281.
6. Kneipp K, Kneipp H, Itzkan I, Dasari R R, Feld M S. Chem. Phys. 1999; 247:155.
7. Xu H, Bjerneld E J, K all B orjesson ML. Phys. Rev. Lett. 1999; 83: 4357.
8. Bjerneld E J, Johansson P, K all M. Single Mol. 2000; 1, 329.
9. Kelly, K. L.; Coronado, E.; Zhao, L. L.; Schatz, G. C. J. Phys. Chem. B 2003, 298, 668-677.
10. Wiens, R. C.; Sharma, S. K.; Thompson, J. et al. Spectrochim. Acta A 2005, 61, 2324-2334.
11. Carter J C, Angel S M, Lawrence-Snyder M, et al., Appl. Spectrosc. 2005, 59, 769.
12. Carter J C, Scaffidi J, Burnett S, et al., Spectrochim Acta A 2005, 61, 2288.
13. Wu M, Ray M, Fung K H, et al., Appl. Spectrosc. 2000, 54, 800-806.

EXAMPLES

The following examples are provided for illustrative purposes only and are not intended to limit the scope of the invention.

Example 1

Experimental Procedure 30 ml of 50 nm diameter gold colloid ($4\times10^{10}$ particles/ml) was diluted with 30 ml of MQ water. A stirring bar (freshly washed with aqua regia) was added. Then 300 ul of polyvinylpyrrolidone solution (pvp, Mw=10000, 2.5 wt % in water) was added slowly while stirring. The mixture was gently stirred at room temperature for 24 h.

The pvp coated particles were transferred to dichloromethane as follows: the aqueous colloid was centrifuged at 3600 rpm for 2 hr. The supernatant was discarded and 60 ml of ethanol was then added. The particles were resuspended in ethanol by ultrasound. The centrifugation and solvent change was carried out for a second time. The resulting ethanolic dispersion was centrifuged, and after discarding the ethanol, 60 ml of dichloromethane was added and the particles redispersed by ultrasound. Centrifugation and addition of fresh dichloromethane was done one more time. Two aliquots of 10 ml each were taken from the final dichloromethane dispersion. To one of the aliquots it was added 500 ul of a 1M solution of pyridine in dichloromethane. To the second aliquot it was added 500 ul of a 1M solution of 4,4'-dipyridyl in dichloromethane. After 48 hr SERS was taken of both samples (FIG.5)

Figure 7:
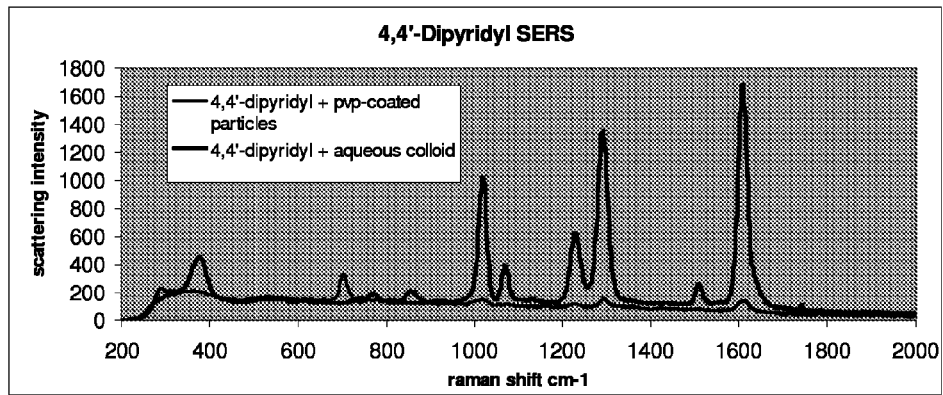
FIG. 7 is a graph of the SERS response of particles having permselective coatings in accordance with the present invention.

FIG. 5 clearly shows that pyridine penetrates the pvp coating and reaches the surface of the particle, resulting in enhanced Raman spectrum, while the larger 4,4'-dipyridyl does not. Knowing that 4,4'-dipyridyl shows a much larger SERS than pyridine when added to aqueous citrate colloids, it is reasonable to conclude that the results using pvp coated particles in dichloromethane are caused by size selective permeation by the polymer layer. Additional data is presented in FIGS. 6 and 7.

What is claimed is:

1. A composition of matter comprising:
   a particle having a spectroscopy-active outer region; and
   a permselective film associated with at least a portion of the particle which selectively allows for specific molecules to reach the outer region of the particle and produce a spectrum when illuminated.

2. The composition of matter of claim 1, wherein the particle comprises a metal.

3. The composition of matter of claim 2, wherein said metal is selected from the group consisting of Au, Ag, Cu, Na, K, Cr, Al, and Li.

4. The composition of matter of claim 1 wherein the permselective film is selected from the group consisting of a globular polymer, a hyperbranched polymer, polydimethylsiloxane, and a porous glass film.

5. The composition of matter of claim 1 wherein the particle is a metal nanoparticle.

6. The composition of matter of claim 5, wherein said metal nanoparticle has a diameter less than about 200 nm.

7. The composition of matter of claim 6, wherein said metal nanoparticle has a diameter between about 20 nm and about 200 nm.

8. The composition of matter of claim 7, wherein said metal nanoparticle has a diameter between about 40 nm and about 100 nm.

9. The composition of matter of claim 1, wherein said permselective film has a thickness of about 10 nm.

10. The composition of matter of claim 1, wherein said permselective film has a thickness less than 10 nm.

* * * * *